United States Patent [19]

Cox

[11] Patent Number: 5,693,952
[45] Date of Patent: Dec. 2, 1997

[54] OPTICALLY CONTROLLED HIGH-VOLTAGE SWITCH FOR AN IMPLANTABLE DEFIBRILLATOR

[75] Inventor: Timothy J. Cox, Lake Jackson, Tex.

[73] Assignee: Sulzer Intermedics Inc., Angleton, Tex.

[21] Appl. No.: 574,353

[22] Filed: Dec. 18, 1995

[51] Int. Cl.⁶ .................. H03K 3/42; A61N 1/39
[52] U.S. Cl. .............. 250/551; 327/514; 327/434; 607/5
[58] Field of Search .................. 250/551, 552, 250/553, 214.1, 214 R, 214 LS, 214 SW; 327/514, 427, 434, 435, 437; 607/5, 6, 7, 8

[56] References Cited

U.S. PATENT DOCUMENTS

| | | | |
|---|---|---|---|
| 4,240,088 | 12/1980 | Myers | 357/19 |
| 4,539,480 | 9/1985 | Artinano et al. | 250/551 |
| 4,564,770 | 1/1986 | Sherman et al. | 250/551 |
| 4,611,123 | 9/1986 | McDonald | 250/551 |
| 4,635,639 | 1/1987 | Hakala et al. | 128/419 D |
| 4,665,316 | 5/1987 | Hodges | 250/551 |
| 4,674,509 | 6/1987 | DeCote, Jr. | 128/419 PT |
| 4,777,387 | 10/1988 | Collins | 250/551 |
| 4,801,821 | 1/1989 | Prevost et al. | 250/551 |
| 4,804,866 | 2/1989 | Akiyama | 250/551 |
| 4,850,357 | 7/1989 | Bach, Jr. | 607/7 |
| 4,864,126 | 9/1989 | Walters et al. | 250/551 |
| 4,902,901 | 2/1990 | Pernyeszi | 250/551 |
| 4,939,375 | 7/1990 | Walters et al. | 250/551 |
| 4,963,729 | 10/1990 | Spillman et al. | 250/551 |
| 4,967,748 | 11/1990 | Cohen | 128/419 D |
| 5,089,948 | 2/1992 | Brown et al. | 363/58 |
| 5,105,090 | 4/1992 | Miyajima et al. | 250/551 |
| 5,163,427 | 11/1992 | Keimel | 607/5 |
| 5,189,307 | 2/1993 | Fabian | 250/551 |
| 5,265,588 | 11/1993 | Nelson et al. | 607/5 |
| 5,267,564 | 12/1993 | Barcel et al. | 128/634 |
| 5,283,441 | 2/1994 | Fabian | 250/551 |
| 5,470,341 | 11/1995 | Kuehn et al. | 607/5 |
| 5,543,627 | 8/1996 | Huggins | 250/551 |

FOREIGN PATENT DOCUMENTS 0 647 456 A1  12/1994  European Pat. Off.

Primary Examiner—Edward P. Westin
Assistant Examiner—John R. Lee
Attorney, Agent, or Firm—John R. Merkling

[57] ABSTRACT

An optically-controlled high-voltage switch for an implantable defibrillator. A three-terminal high-voltage-tolerant semiconductor switch exhibits high conductivity between its high-voltage terminal and its common terminal in response to a low control voltage applied between its control terminal and its common terminal, where the low control voltage exceeds a characteristic threshold value, and exhibits low conductivity between same where the control voltage is less than the characteristic threshold value. A photovoltaic coupler/isolator having a light emitting device and a photovoltaic device, optically coupled to and electrically isolated from each other, is in circuit communication across the control and common terminals. A low voltage current source drives the light emitting device of the photovoltaic coupler/isolator. A switch-off opto-isolator having a light emitting device and a light sensitive conductive device, optically coupled to and electrically isolated from each other, is in circuit communication across the control and common terminals of the semiconductor switch. A switch-off low voltage current source drives the light emitting device of the switch-off opto-isolator. A switch-on opto-isolator having a light emitting device and a light sensitive conductive device, optically coupled and electrically isolated from each other, is in series circuit communication between the photovoltaic device and the semiconductor switch. A switch-on low voltage current source drives the light emitting device of the switch-on opto-isolator.

14 Claims, 3 Drawing Sheets

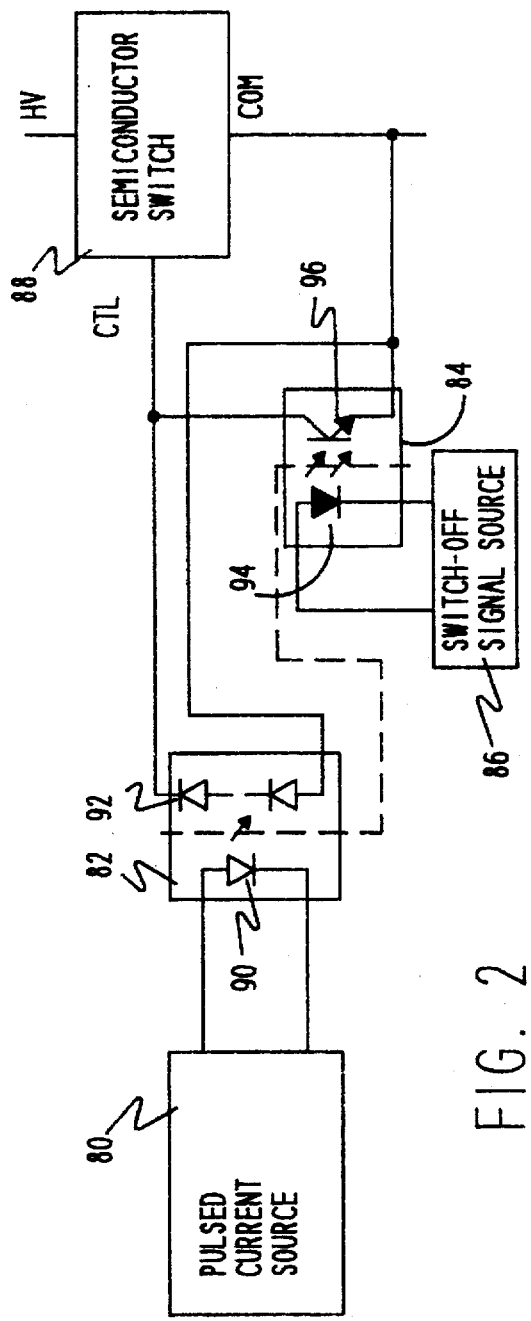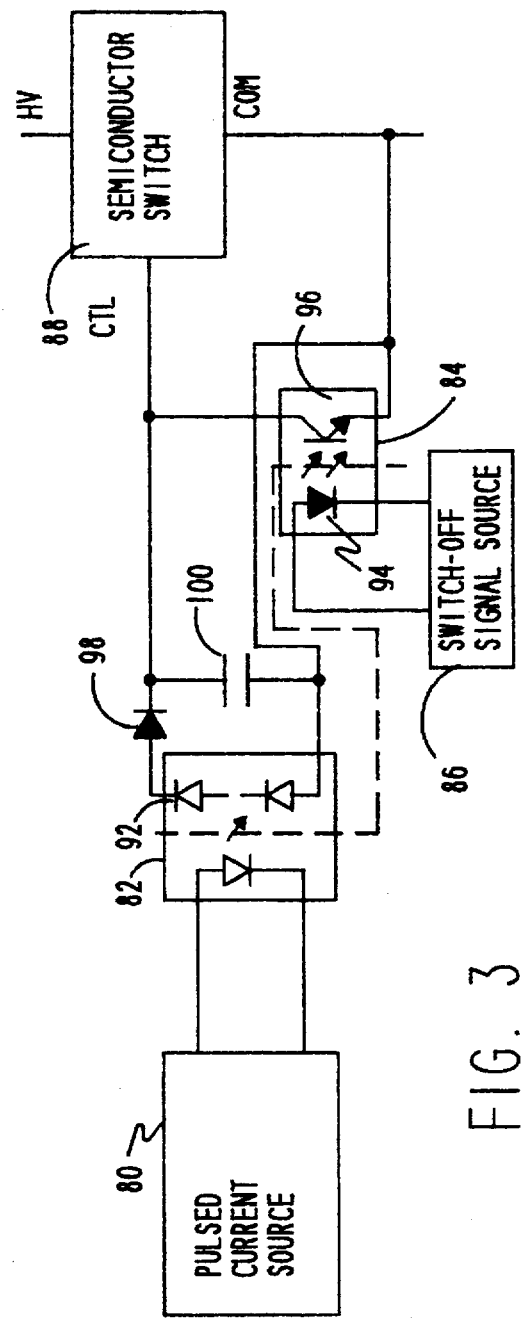
FIG. 2
FIG. 3

OPTICALLY CONTROLLED HIGH-VOLTAGE SWITCH FOR AN IMPLANTABLE DEFIBRILLATOR

FIELD OF THE INVENTION

The present invention relates generally to implantable cardiac stimulators, and more particularly to circuitry in such devices for switching high voltages between a storage capacitor and a defibrillation electrode.

BACKGROUND ART

Present implantable defibrillators are designed to constantly sense intra-cardiac electrogram signals and, upon sensing signal patterns indicative of fibrillation, automatically deliver defibrillation therapy. Such therapy typically includes the application of high voltage, high energy shocks to cardiac tissue via implanted defibrillation leads and electrodes. Implantable defibrillators, being battery powered devices, cannot provide electrical shocks directly from the power source at the high energy levels that are required. It is therefore conventional to step up the voltage from the battery by applying a switched DC voltage to the primary winding of a transformer, rectifying the resulting high voltage AC output from the secondary winding of the transformer, and charging a high-voltage storage capacitor with the rectified high voltage. The shock is generated by switching the terminals of the high-voltage storage capacitor into electrical contact with the defibrillation leads and discharging the capacitor through the leads, electrodes, and, ultimately, cardiac tissue. It is therefore necessary to provide switching circuits in the implantable defibrillator, controlled by low voltage circuits, for switching the high voltages.

A biphasic shock waveform can reduce the threshold energy level necessary for successful defibrillation. The biphasic waveform can be generated by initially discharging the stored energy in one direction between a pair of defibrillation electrodes, followed by a switched reversal of direction during the course of the discharge. Alternatively, the discharge path can be switched during the course of the discharge by disconnecting the initial pair of electrodes from the storage capacitor and connecting a different second pair of electrodes. The second pair of electrodes may or may not share a common electrode with the first pair of electrodes.

Either type of switching can be accomplished with an electronic circuit known as a bridge, including four or more semiconductor switch components constructed to tolerate the highest voltage of the stored energy. Each semiconductor switch is typically characterized as having three terminals: a common terminal, a control terminal and a high voltage tolerant terminal, which may be designated COM, CTL and HV, respectively. The common terminal (COM) is a reference for the control terminal (CTL) and the high voltage terminal (HV). The semiconductor switch components may be MOSFETs, IGBTs (insulated gate bipolar transistors) or MCTs (MOS-controlled thyristers). Other devices are feasible also, such as bipolar transistors and GTO (gate-turn-off) thyristers, at the cost of greater energy losses.

SUMMARY OF THE INVENTION

It is an object of the present invention to control high-voltage switching circuitry in an implantable medical device, using low-voltage control circuitry, with only optical coupling between the low-voltage and high-voltage circuitry, and without substantial conductive, capacitive or magnetic coupling between the low-voltage and high voltage circuitry.

The invention has the advantage of greater isolation in a smaller physical volume, between the low- and high-voltage sides, than can be accomplished with transformer coupling, with excellent noise immunity, and with shorter turn-on and turn-off transition times than can be accomplished with conventional solid state photovoltaic relays.

In accordance with one aspect of the present invention, an optically-controlled high-voltage switch for an implantable defibrillator includes a three-terminal high-voltage-tolerant semiconductor switch having a high-voltage terminal, a common terminal, and a control terminal, and a photovoltaic coupler/isolator in circuit communication across the control and common terminals of the semiconductor switch. A low voltage current source is in circuit communication with a light emitting device of the photovoltaic coupler/isolator. A switch-off opto-isolator is in circuit communication across the control and common terminals of the semiconductor switch. A switch-off low voltage current source is in circuit communication with a light emitting device of the switch-off opto-isolator.

Other aspects, objects and advantages of the present invention will be apparent from the following descriptions made with reference to the drawings.

BRIEF DESCRIPTION OF THE DRAWINGS

FIG. 2 is a schematic illustration of one embodiment of a high-voltage semiconductor switch of the bridge circuit of FIG. 1 together with optical isolation circuitry for isolating the high-voltage switch from the low-voltage control circuitry of the defibrillator.

FIG. 3 is an alternative embodiment of the circuitry of FIG. 2.

DETAILED DESCRIPTION OF THE PREFERRED EMBODIMENTS

Figure 1:
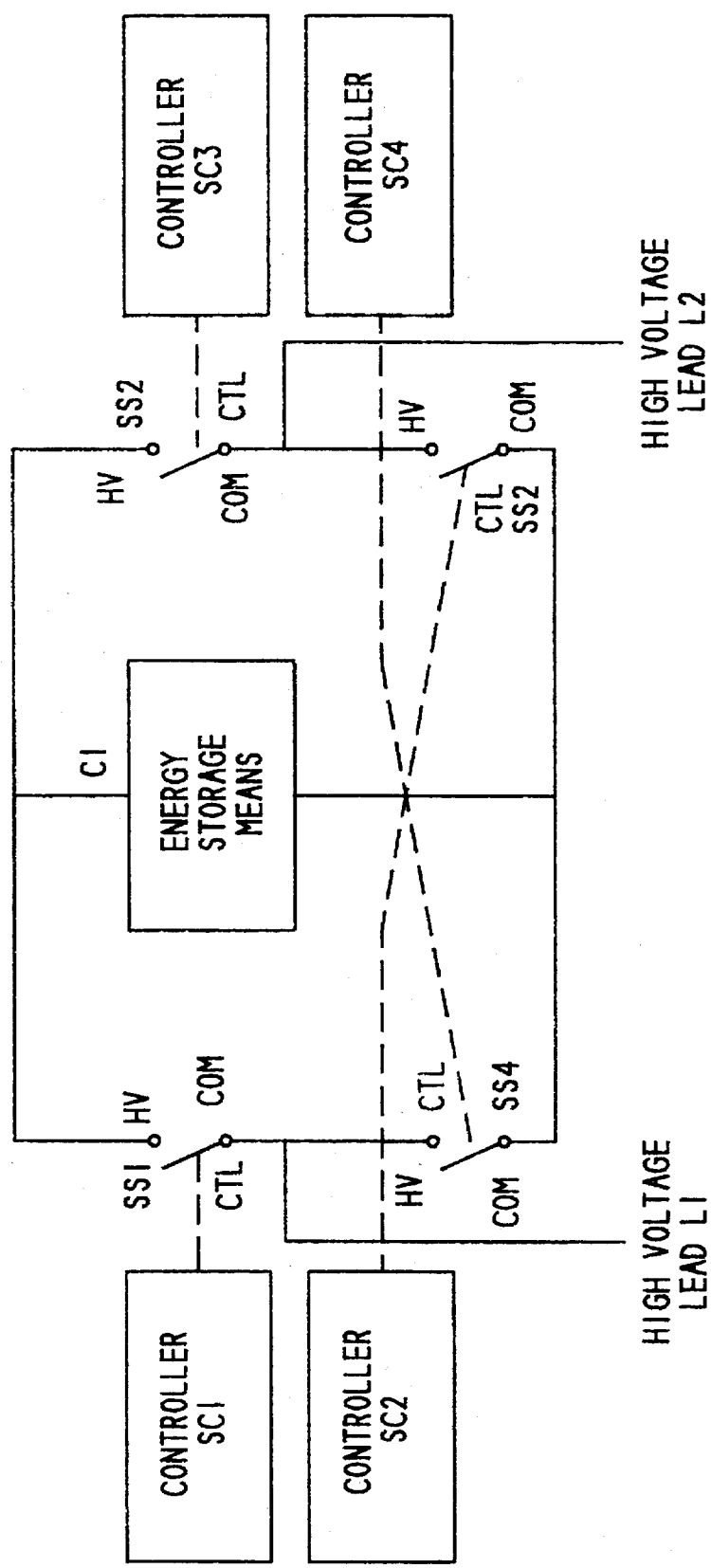
FIG. 1 is a schematic illustration of a bridge circuit that is useful in an implantable defibrillator for switching high voltages between a storage capacitor and high-voltage defibrillation leads.

In one of its simplest forms, the bridge of an implantable defibrillator may include four semiconductor switches, SS1–SS4, arranged as shown in FIG. 1. The energy storage means C1 is commonly a capacitor sustaining a high voltage after being charged up by conventional voltage step-up and capacitor charging circuits. In operation, switch controllers SC1 and SC2 close semiconductor switches SS1 and SS2, respectively, simultaneously. As a result, lead L1, which is connected to an implanted defibrillation electrode, is raised to a high voltage with respect to lead L2, which is connected to another implanted defibrillation electrode. The high voltage differential between L1 and L2 diminishes over time as current flows into the cardiac tissue. At some later time controllers SC1 and SC2 open semiconductor switches SS1 and SS2 before all the energy has been discharged from capacitor C1. Thereafter, switch controllers SC3 and SC4 close switches SS3 and SS4, respectively, simultaneously, so that current flows from capacitor C1 along leads L1 and L2 in the opposite direction. Still later, controllers SC3 and SC4 open switches SS3 and SS4.

As switches SS1 and SS2 are closed, the voltage between the respective HV and COM terminals of each switch SS1 and SS2 collapses almost to zero. Simultaneously, as switches SS3 and SS4 are opened, the voltage between the respective HV and COM terminals of each switch SS3 and SS4 increases almost to the full voltage across C1. For that reason, it is undesirable to use the HV to COM voltages as DC supplies for the controllers SC1–SC4, as the components necessary to avoid transient feedback effects during switching (while withstanding the high voltage for a significant period of time) would have substantial physical size, deleteriously affecting the overall size of the implantable device. A preferable approach, therefore, is to provide power to the switch controllers SC1–SC4 from the stable, regulated low voltage power supply of the implantable defibrillator that is used to provide power to other control and sensing circuitry. Such an approach demands, however, that the high voltage circuitry be effectively and reliably isolated from the low voltage circuitry to avoid damage to any of the components of the low voltage circuitry. The present invention provides such desirable voltage isolation and provides other desirable advantages.

Referring to FIG. 2, there is illustrated one embodiment of the present invention wherein the controller SC1 of FIG. 1 includes a pulse current source 1, a photovoltaic coupler/isolator 2 (such as a commercially available device, type DIG11-15-3000), an opto-isolator 3 (such as a commercially available device, type 4N35), and a "switch-off" signal source 4. The semiconductor switch SS1 of FIG. 1 comprises a three-terminal high-voltage semiconductor switch 5 (such as a commercially available IGBT device, type IRGPH40F). Each of the other controllers SC2, SC3 and SC4, and the other semiconductor switches SS2, SS3 and SS4 are comprised of similar circuitry and components. Pulse current source 1 is electrically connected across a pair of terminals of an internal light-emitting device 6 of photovoltaic coupler/isolator 2. A pair of terminals of an internal array of photovoltaic devices 7 of photovoltaic coupler/isolator 2 are connected across the CTL and COM terminals of the semiconductor switch 5. Devices 6 and 7 are electrically isolated from each other on opposite sides of a low-voltage to high-voltage barrier VB. Switch-off signal source 4 is connected across a pair of terminals of an internal light-emitting device 8 of opto-isolator 3. A pair of terminals of an internal light-sensitive device 9 of opto-isolator 3 are connected across the CTL and COM terminals of the semiconductor switch 5, in parallel with the internal array of photovoltaic devices 7 of photovoltaic coupler/isolator 2. Devices 8 and 9 are electrically isolated from each other on opposite sides of the low-voltage to high-voltage barrier VB.

To close semiconductor switch 5, pulse current source 1 forces current through light-emitting device 6, causing device 6 to emit light and illuminate photovoltaic device 7, which in turn generates electrical current that flows into the CTL terminal of the semiconductor switch 5, causing an increase of voltage across the CTL and COM terminals. As the CTL to COM voltage reaches a predetermined threshold that is characteristic of semiconductor switch 5, the semiconductor switch 5 turns on, or enters a state of high conductivity between the HV and COM terminals. After switch 5 turns on, pulse current source 1 is switched off.

To open semiconductor switch 5, switch-off signal source 4 is activated. Signal source 4 forces current through light-emitting device 8, causing device 8 to emit light and illuminate light-sensitive device 9, which can be a light-sensitive resistor, an opto-diode or an opto-transistor. As a result, a path of high conductivity is made between the CTL and COM terminals of semiconductor switch 5 through light-sensitive device 9, such that the voltage between the CTL and COM terminals falls below the threshold that is necessary to keep semiconductor switch 5 turned on. Semiconductor switch 5 therefore turns off, or enters a state of low conductivity between the HV and COM terminals.

One limitation of the embodiment of FIG. 2 is that photovoltaic device 7 of the photovoltaic coupler/isolator 2 may not be optimized to inhibit current leakage therethrough in the reverse direction, i.e., from CTL to COM, when pulsed current source 1 is turned off, thereby limiting the maximum time that the voltage between CTL and COM stays above the threshold that is required to maintain semiconductor switch 5 in a state of conduction. That limitation could be compensated for by maintaining current from pulse current source 1 beyond the time when the turn-on threshold of semiconductor switch 5 is reached, but at the cost of additional energy consumption that would decrease the life of the battery.

Another limitation of the embodiment of FIG. 2 is that the impedance between terminals CTL and COM within semiconductor switch 5, while high, is not infinite, resulting in a further leakage path that limits the maximum time that semiconductor switch 5 can remain in a state of conduction after pulsed current source 1 is turned off.

In FIG. 3, there is illustrated an improved embodiment that addresses the two limitations of the embodiment of FIG. 2 described above. In particular, reverse leakage through photovoltaic device 7 is reduced by providing a separate diode 10 in series with photovoltaic device 7 between photovoltaic coupler/isolator 2 and terminal CTL of semiconductor switch 5. Furthermore, reverse leakage between terminals CTL and COM within semiconductor switch 5 is partially compensated for by providing a capacitor 11 across terminals CTL and COM. Capacitor 11 stores more energy than would be stored in semiconductor switch 5 alone, and therefore allows switch 5 to remain in a state of conduction for a longer period of time, given the leakage path between CTL and COM, than would otherwise be the case.

Another limitation of the above-described embodiments is the result of the slow rate of response of contemporary photovoltaic devices such as photovoltaic coupler/isolator 2. That slow rate of response can cause semiconductor switch 5 to make a slow transition between its low and high conductivity states, during which transition it may absorb excessive energy resulting in a reduced life or complete destruction.

Figure 4:
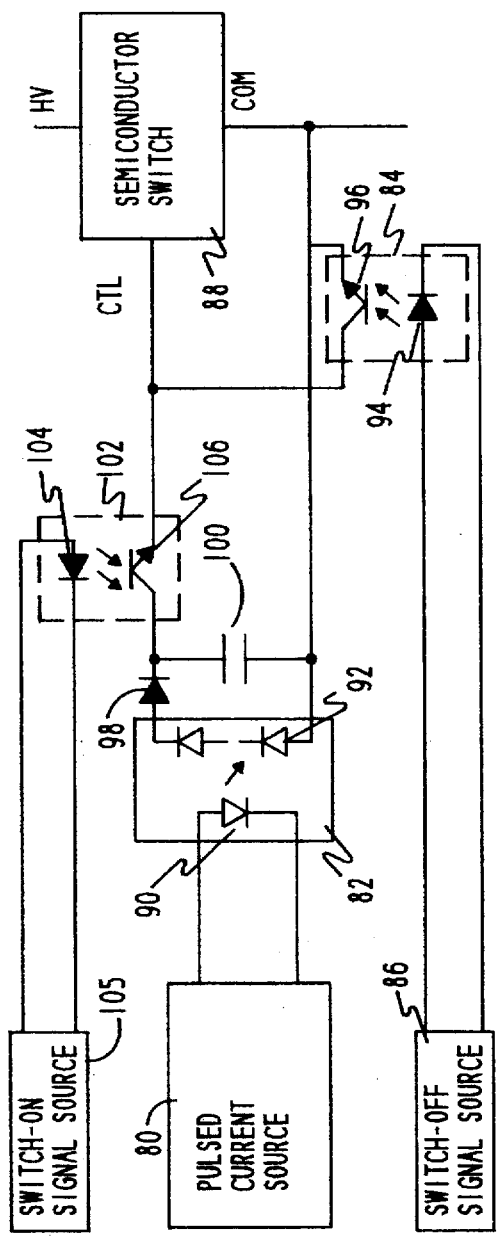
FIG. 4 is another alternative embodiment of the circuitry of FIG. 2.

In FIG. 4, there is shown an improved embodiment that eliminates the restriction on switching time set by photovoltaic coupler/isolator 2. The energy produced at the output of photovoltaic device 7 is stored in capacitor 11, which is isolated from the CTL terminal of semiconductor switch 5 by a second opto-isolator 12 that is in a state of low conductivity. The storage of energy is accompanied by a rise of voltage across capacitor 11. The voltage continues to rise until it exceeds the value of the threshold of semiconductor switch 5. At that point, the pulse current source 1 would be switched off. Thereafter, "switch-on" signal source 13 is activated to force current through light-emitting device 14, causing device 14 to emit light and illuminate light-sensitive device 15, which can be a light-sensitive resistor, an opto-diode or an opto-transistor. As a result, a path of high conductivity is made between capacitor 11 and terminal CTL, causing charge to be transferred from capacitor 11 to the CTL input of semiconductor switch 5. Consequently, semiconductor switch 5 is turned on. Opto-isolator 12 is chosen for fast switching from its low to high conductivity states, although the switching in the opposite order need not be as fast. When it is required to switch off semiconductor switch 5, "switch-off" signal source 4 is activated to switch opto-isolator 3 to a state of high conductivity, thereby depleting the charge on both capacitor 11 and the CTL terminal of semiconductor switch 5. The voltage between terminals CTL and COM quickly falls below the threshold necessary to maintain switch 5 in a state of high conductivity between terminals HV and COM, and switch 5 is turned off. Opto-isolator 3 is chosen for fast switching from its low to high conductivity states, although the switching in the opposite order need not be as fast.

Referring again to FIG. 1, whenever switch SS1 or SS3 is switched on first relative to switch SS4 or SS2, respectively, switch SS4 or SS2 experiences a rapidly rising voltage between its HV to COM terminals. Due to capacitive coupling between the HV and COM terminals, this transient voltage gives rise to an inappropriate voltage across the CTL and COM terminals of switch SS4 or SS2. This CTL to COM voltage can reach the threshold of activation for the switch SS4 or SS2, resulting in switch SS4 or SS2 being switched on simultaneously with switch SS1 or SS3, thereby "shorting" the energy storage means C1 and causing damage to or destruction of switches SS1 and SS4, or switches SS3 and SS2, due to their power dissipation capacity being exceeded.

Figure 5:
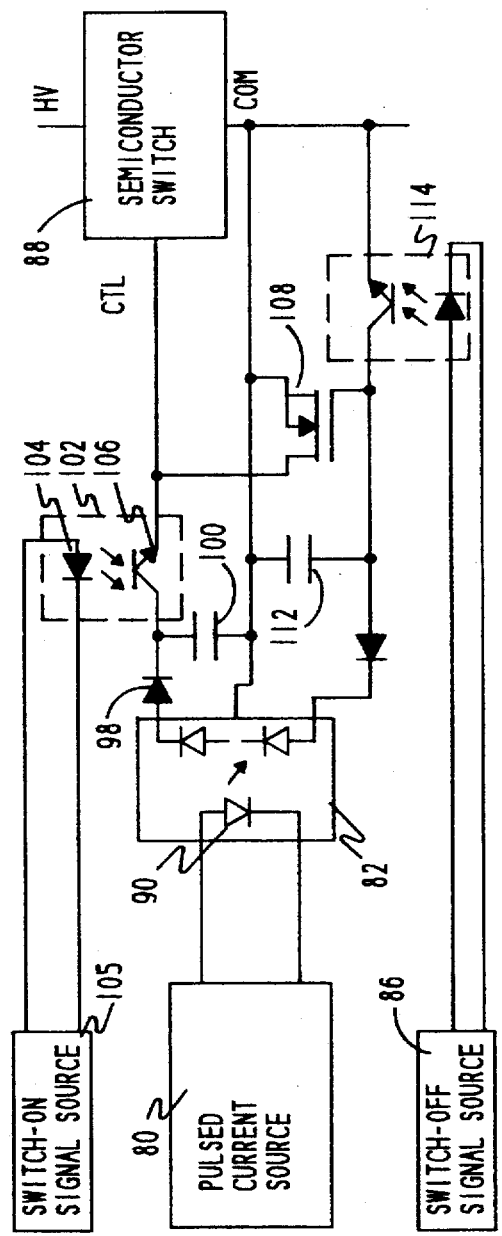
FIG. 5 is a further alternative embodiment of the circuitry of FIG. 2.

In FIG. 5, there is illustrated a further embodiment in which protection is provided for semiconductor switch 5 to prevent it from being switched on unintentionally due to voltage transients between the HV and COM terminals giving rise to an unwanted, and possibly threshold-exceeding, voltage between the CTL and COM terminals, as discussed above. The embodiment of FIG. 5 differs from that of FIG. 4 in that opto-isolator 3 is replaced by a depletion mode MOSFET 16 having its drain terminal D connected to the CTL terminal of switch 5, and having its source terminal S connected to the COM terminal of switch 5. MOSFET 16 remains in a state of high conductivity between its source S and drain D terminals so long as zero voltage is applied between its gate G and source S terminals, thereby "shorting" the CTL and COM terminals of switch 5 and protecting switch 5 from being switched on unintentionally. Also, the COM terminal, rather than being connected to the bottom end of the photovoltaic array 7, is connected to the middle of the array. The bottom end of the photovoltaic array 7 is connected through diode 17 to the gate terminal G of MOSFET 16, and a further capacitor 18 is connected across the source S and drain D terminals of MOSFET 16. An opto-isolator 19, similar to opto-isolator 3 of FIG. 4, has an input connected to switch-off signal source 4 and an output connected across the source S and gate G terminals of MOSFET 16.

To disable the protection of semiconductor switch 5, in preparation for turning switch 5 on, the pulse current source 1 is activated, giving rise to a positive voltage at the upper end of photovoltaic array 7 relative to the COM terminal, as before. A negative voltage is generated at the bottom end of photovoltaic array 7, relative to the COM terminal, causing diode 17 to conduct and causing a negative voltage to build up across capacitor 18 relative to the COM terminal, and at the gate G relative to source S of MOSFET 16. The negative gate to source voltage causes MOSFET 16 to be less conductive between its drain D and source S terminals. Eventually, MOSFET 16 becomes in effect a high value resistor between the CTL and COM terminals, thereby disabling the protection of switch 5. After the pulse current source 1 has been switched off, the voltage across capacitor 18 maintains MOSFET 16 in its "off" state as switch 5 is turned on and until switch 5 is turned off again. As before, opto-isolator 12 is activated by switch-on signal source 13, thereby connecting capacitor 11 across the CTL and COM terminals to turn on switch 5.

To turn off switch 5, opto-isolator 19 is activated by switch-off signal source 4, thereby making a path of high conductivity across capacitor 18 and between source S and gate G of MOSFET 16 and removing the voltage between source S and gate G so that MOSFET 16 again enters a state of high conductivity between its drain D and source S terminals. Consequently, the voltage between the CTL and COM terminals, and across capacitor 11, quickly falls below the activation threshold of switch 5, and switch 5 enters a state of low conductivity between its HV and COM terminals.

The present invention has been described with particularity in terms of a preferred embodiments, by way of illustration and not limitation. The scope of the invention is defined by the claims appended hereto. Variations of the particular embodiments described herein that incorporate the principles of the present invention may still fall within the scope of the appended claims.

I claim:

1. An optically-controlled high-voltage switch for an implantable defibrillator, comprising:

a three-terminal high-voltage-tolerant semiconductor switch having a high-voltage terminal, a common terminal, and a control terminal, and exhibiting high conductivity between said high-voltage terminal and said common terminal in response to a low control voltage applied between said control terminal and said common terminal, where said low control voltage exceeds a characteristic threshold value, and exhibiting low conductivity between said high-voltage terminal and said common terminal when the voltage between said control terminal and said common terminal is less than said characteristic threshold value;

a photovoltaic coupler/isolator having a light emitting device and a photovoltaic device, in which said light emitting device is optically coupled to and electrically isolated from said photovoltaic device, said photovoltaic device being in circuit communication across said control and common terminals of said semiconductor switch;

low voltage current source means in circuit communication with said light emitting device of said photovoltaic coupler/isolator for driving said light emitting device;

a capacitor in circuit communication across said control and common terminals of said semiconductor and across said photovoltaic device:

a switch-on opto-isolator having a light emitting device and a light sensitive conductive device, in which said light emitting device is optically coupled to and electrically isolated from said light sensitive conductive device, and in which said light sensitive device exhibits low conductivity when not illuminated and exhibits high conductivity when illuminated, said light sensitive conductive device being in series circuit communication between said capacitor and said semiconductor switch; and switch-on low voltage current source means in circuit communication with said light emitting device of said switch-on opto-isolator for driving said light emitting device;

a switch-off opto-isolator having a light emitting device and a light sensitive conductive device, in which said light emitting device is optically coupled to and electrically isolated from said light sensitive conductive device, and in which said light sensitive device exhibits low conductivity when not illuminated and exhibits high conductivity when illuminated, said light sensitive conductive device being in circuit communication across said control and common terminals of said semiconductor switch; and switch-off low voltage current source means in circuit communication with said light emitting device of said switch-off opto-isolator for driving said light emitting device.

2. The optically-controlled high-voltage switch of claim 1, and further including:
    a diode in series circuit communication between said photovoltaic device and said semiconductor switch to alleviate reverse current flow through said photovoltaic device when not illuminated.

3. An optically-controlled high-voltage switch for an implantable defibrillator, comprising:
    a three-terminal high-voltage-tolerant semiconductor switch having a high-voltage terminal, a common terminal, and a control terminal, and exhibiting high conductivity between said high-voltage terminal and said common terminal in response to a low control voltage applied between said control terminal and said common terminal, where said low control voltage exceeds a characteristic threshold value, and exhibiting low conductivity between said high-voltage terminal and said common terminal when the voltage between said control terminal and said common terminal is less than characteristic threshold value;
    a photovoltaic coupler/isolator having a light emitting device and a photovoltaic device, in which said light emitting device is optically coupled to and electrically isolated from said photovoltaic device, said photovoltaic device having a first output terminal, a second output terminal and a common output terminal and configured to generate voltage of opposite polarity at said first and second output terminals relative to said common output terminal, said first and second output terminals being in circuit communication across said control and common terminals of said semiconductor switch;
    low voltage current source means in circuit communication with said light emitting device of said photovoltaic coupler/isolator for driving said light emitting device;
    protection means for preventing said semiconductor switch from being turned on inadvertently by transient signals coupled between said high-voltage and control terminals, said protection means comprising a depletion-mode MOSFET having gate, source and drain terminals, with said source and drain terminals connected across said control and common terminals of said semiconductor switch, and with said gate terminal being in circuit communication with said second output terminal of said photovoltaic device;
    a switch-off opto-isolator having a light emitting device and a light sensitive conductive device, in which said light emitting device is optically coupled to and electrically isolated from said light sensitive conductive device, and in which said light sensitive device exhibits low conductivity when not illuminated and exhibits high conductivity when illuminated, said light sensitive conductive device being in circuit communication across said gate terminal of said depletion-mode MOSFET and said common terminal of said semiconductor switch; and a switch-off low voltage current source means in circuit communication with said light emitting device of said switch-off opto-isolator for driving said light emitting device.

4. The optically-controlled high-voltage switch of claim 3, and further including:
    a diode in series circuit communication between at least one of said first and second output terminals of said photovoltaic device and said semiconductor switch to alleviate reverse current flow through said photovoltaic device when not illuminated.

5. The optically-controlled high-voltage switch of claim 4, and further including:
    a capacitor in circuit communication across said control and common terminals of said semiconductor switch to compensate for charge leakage between said control and common terminals within said semiconductor switch.

6. The optically-controlled high-voltage switch of claim 3, and further including:
    a capacitor in circuit communication across said gate and source terminals of said depletion-mode MOSFET.

7. The optically-controlled high-voltage switch of claim 4, and further including:
    a capacitor in circuit communication across said gate and source terminals of said depletion-mode MOSFET.

8. The optically-controlled high-voltage switch of claim 5, and further including:
    a capacitor in circuit communication across said gate and source terminals of said depletion-mode MOSFET.

9. The optically-controlled high-voltage switch of claim 3, and further including:
    a switch-on opto-isolator having a light emitting device and a light sensitive conductive device, in which said light emitting device is optically coupled to and electrically isolated from said light sensitive conductive device, and in which said light sensitive device exhibits low conductivity when not illuminated and exhibits high conductivity when illuminated, said light sensitive conductive device being in series circuit communication between said photovoltaic device and said semiconductor switch; and
    a switch-on low voltage current source means in circuit communication with said light emitting device of said switch-on opto-isolator for driving said light emitting device.

10. The optically-controlled high-voltage switch of claim 9, and further including:
    a diode in series circuit communication between at least one of said first and second output terminals of said photovoltaic device and said semiconductor switch to alleviate reverse current flow through said photovoltaic device when not illuminated.

11. The optically-controlled high-voltage switch of claim 10, and further including:
    a capacitor in circuit communication across said control and common terminals of said semiconductor switch to compensate for charge leakage between said control and common terminals within said semiconductor switch.

12. The optically-controlled high-voltage switch of claim 9, and further including:
    a capacitor in circuit communication across said gate and source terminals of said depletion-mode MOSFET.

13. The optically-controlled high-voltage switch of claim 10, and further including:

a capacitor in circuit communication across said gate and source terminals of said depletion-mode MOSFET.

14. The optically-controlled high-voltage switch of claim 11, and further including:

a capacitor in circuit communication across said gate and source terminals of said depletion-mode MOSFET.

* * * * *